(12) United States Patent
Lienau et al.

(10) Patent No.: US 6,548,256 B2
(45) Date of Patent: Apr. 15, 2003

(54) DNA ISOLATION METHOD AND KIT

(75) Inventors: E. Kurt Lienau, Rhinebeck, NY (US); J. Michael Hurley, Louisville, CO (US)

(73) Assignee: Eppendorf 5 Prime, Inc., Boulder, CO (US)

( * ) Notice: Subject to any disclaimer, the term of this patent is extended or adjusted under 35 U.S.C. 154(b) by 0 days.

(21) Appl. No.: 09/906,898

(22) Filed: Jul. 16, 2001

(65) Prior Publication Data

US 2002/0072110 A1 Jun. 13, 2002

Related U.S. Application Data

(60) Provisional application No. 60/218,328, filed on Jul. 14, 2000.

(51) Int. Cl.$^7$ .......................... C12Q 1/68; C12P 19/34; C07H 21/02; C07H 21/04
(52) U.S. Cl. ......................... 435/6; 435/91.2; 536/23.1
(58) Field of Search .................... 435/6, 91.2; 536/23.1

(56) References Cited

U.S. PATENT DOCUMENTS

| | | | |
|---|---|---|---|
| 4,921,805 A | 5/1990 | Gebeyehu et al. | 435/270 |
| 4,935,342 A | 6/1990 | Seligson et al. | 435/6 |
| 5,010,183 A | 4/1991 | Macfarlane | 536/27 |
| 5,234,809 A | 8/1993 | Boom et al. | 435/91 |
| 5,898,071 A | 4/1999 | Hawkins | 536/25.4 |
| 5,945,515 A | 8/1999 | Chomczynski | 530/412 |

OTHER PUBLICATIONS

Reek et al., "Use of Multiscreen Plates for the Preparation of Bacterial DNA Suitable for PCR", BioTechniques, vol. 19, No. 2, pp. 282–285 (1995).*

Search History.

* cited by examiner

Primary Examiner—Kenneth R. Horlick
Assistant Examiner—Teresa Strzelecka
(74) Attorney, Agent, or Firm—Dorsey & Whitney LLP

(57) ABSTRACT

A method and kit for isolating nucleic acids from a nucleic acid containing starting material is disclosed, where the nucleic acids are released from the starting material and precipitated onto a trapping membrane. The method and kit may be used in the context of isolating genomic DNA from blood and isolating BACs from transformed bacterial cultures.

42 Claims, 4 Drawing Sheets

DNA ISOLATION METHOD AND KIT

RELATED APPLICATIONS

This application claims the benefit of priority of U.S. Provisional Patent Application Ser. No. 60/218,328 filed Jul. 14, 2000 entitled "PERFECT gDNA ISOLATION KIT AND PERFECT gDNA ISOLATION AND PURIFICATION METHOD."

FIELD OF THE INVENTION

The invention relates to the isolation of nucleic acid from cellular sources, and more particularly the isolation of high molecular weight genomic DNA from biological fluids and bacterial artificial chromosomes from transformed bacterial cultures.

BACKGROUND OF THE INVENTION

Isolated nucleic acid, and in particular, isolated high molecular weight DNA, has a variety of uses in molecular biology, biotechnology and clinical research. For example, isolated DNA is useful in a number of molecular biology techniques, including polymerase chain reaction (PCR), DNA hybridization, restriction enzyme digestion, DNA sequencing, and array-based experiments. With regard to biotechnology, isolated DNA is useful in the development of genetically engineered recombinant proteins and in identifying potential new therapeutic targets. In the clinical setting, isolated DNA is useful in the identification of genetic disorders and in the diagnosis of bacterial and/or viral infections. As such, there is a need for simple and reliable methods for isolating DNA, and in particular, for isolating high quality, high molecular weight DNA.

The most commonly used method for isolating DNA from a DNA source, e.g., blood, saliva, bacterial cultures, etc., involves lysing the DNA source with a combination of a proteolytic enzyme and a detergent followed by extracting the mixture with an organic solvent, e.g., phenol and chloroform, so that the DNA enters the aqueous phase and the hydrolyzed products enter the organic phase. The DNA in the aqueous phase is then precipitated by the addition of alcohol. However, these organic extraction methods are laborious and time consuming and require the use of phenol (or other organic solvents), which are typically toxic and, therefore, a safety hazard.

In another approach, the DNA is isolated by lysing the DNA source with a chaotropic substance, for example guanidinium salt, urea and sodium iodide, in the presence of a DNA binding solid phase. The released DNA is bound to the solid phase in a one step reaction, where the beads are washed to remove any residual contaminants. Although these methods have proven to be less time consuming and toxic, they have resulted in a moderate level of DNA shearing and some level of contamination.

In a further approach, the DNA is isolated from a starting source by mixing the starting source with a cationic detergent, which forms a hydrophobic complex between the DNA and detergent. The hydrophobic complex is separated from the solubilized contaminants and the DNA recovered by addition of a salt. As above, this approach has proven to be much less time consuming, but does result in some level of DNA shearing and contamination. Against this backdrop the present invention has been developed.

SUMMARY OF THE INVENTION

The present invention provides novel methods and kits for the isolation of nucleic acid from a nucleic acid containing starting material. One method of the present invention includes mixing the starting material with a lysing and denaturing substance for release of the nucleic acid from the starting material; separating the mixture into a first portion and a second portion, where the first portion has a greater amount of the nucleic acid than the second portion; adding an alcohol and detergent substance to the first portion to precipitate the nucleic acid onto a nylon membrane; and re-suspending the isolated nucleic acid off of the nylon membrane in a re-suspension buffer.

These and various other features as well as advantages that characterize the invention will be apparent from a reading of the following detailed description and a review of the associated figures.

DETAILED DESCRIPTION OF THE INVENTION

Definitions

Figure 1:
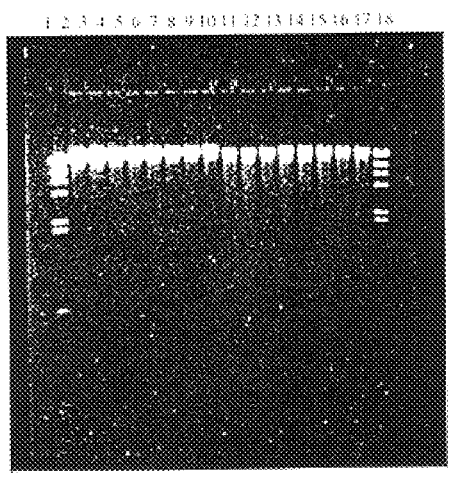
FIG. 1 illustrates gDNA isolated from human blood in accordance with a method of the present invention. Lanes 1 and 18 are λ Hind III Marker, lanes 2–9 are gDNA isolated using methods of the present invention and lanes 10–17 are gDNA isolated using a Qiagen kit.

The followings definitions are provided to facilitate understanding of certain terms used frequently herein and are not meant to limit the scope of the present disclosure.

The term "about" refers to a deviation in the recited value of 5% or less.

The term "isolating" refers to a process for separating a nucleic acid from at least one contaminant with which it is normally associated. In preferred embodiments, isolating refers to separating a nucleic acid from at least 50% of the contaminants with which it is normally associated, and more preferably from at least 75% of the contaminants with which it is normally associated.

The term "high molecular weight DNA" refers to DNA having an average molecular weight of at least 15 kb, and more preferably at least 20 kb, and most preferably at least 23 kb.

The term "membrane" or "trapping membrane" refers to a microporous structure having a pore diameter from 0.2 $\mu$M to 5 $\mu$M, and more preferably from 0.45 $\mu$M to 1.2 $\mu$M, that acts as a platform or surface to trap precipitated nucleic acids and/or to facilitate the precipitation of nucleic acids onto the membrane, while not preferentially absorbing potentially contaminating proteins or other biologic agents, example membranes for use with the present invention include, glass fiber, glass fiber treated with oleophobic coatings, silica particles, nylon, and the like.

The term "nucleic acid" refers to a linear sequence of nucleotides. The nucleotides are either a linear sequence of polyribonucleotides or polydeoxyribonucleotides, or a mixture of both. Examples of nucleic acid in the context of the present invention include—single and double stranded DNA, single and double stranded RNA, and hybrid molecules that have mixtures of single and double stranded DNA and RNA. Further, the nucleic acids of the present invention may have one or more modified nucleotides.

The term "PCR" or "polymerase chain reaction" refers to the process to amplify nucleic acids as described in U.S. Pat. Nos. 4,683,105 and 4,683,202, both owned by Roche Molecular.

The term "rapid" and "rapidly" in reference to the release of the nucleic acid, including BAC, from the trapping membrane refers to a period of less than one hour, and more preferably less than 30 minutes, and most preferably less than 10 minutes.

The term "spin device" refers to a housing that incorporates a trapping membrane of the present invention. The housing fits within a microcentrifuge tube and facilitates the insertion and removal of the trapping membrane from the microcentrifuge tube. In preferred embodiments, the spin device is an extended tube, where a first end of the tube is covered by a trapping membrane of the present invention, and the second end is open to receive samples/fluids useful to the present invention. The first end of the spin device tube is positioned toward the bottom of the microcentrifuge tube and the second end of the spin device tube is positioned toward the top of the microcentrifuge tube.

The term "starting material" refers to any material containing nucleic acid, for example, cell lysates, bacterial cultures, human blood, chicken blood, rodent blood, buffy coat, saliva, urine, etc.

The present invention provides novel methods and kits for the isolation of nucleic acid from a nucleic acid containing starting material. In one preferred aspect, the invention provides methods and kits for the isolation of high molecular weight DNA, typically genomic DNA, from a biologic starting material, e.g., blood, saliva, buffy coat, urine, as well as from cell cultures and the like. Preferably, the invention provides methods and kits for the isolation of DNA where at least 60%, and more preferably at least 70%, and most preferably at least 80%, of the DNA has a molecular weight greater than 20 kb. In another preferred aspect, the invention provides methods and kits for the isolation of intact plasmids, cosmids, and bacterial artificial chromosomes (BACs) from transformed cell cultures, and more preferably provides methods and kits for the isolation of intact BACs from bacterial cultures.

The methods and kits of the present invention are both convenient, i.e., avoid the use of toxic and corrosive solvents, and rapid, i.e., typically isolate nucleic acids in less than 30 minutes. The majority of the isolated nucleic acid is in undamaged condition and has a high degree of purity. The method allows for the direct use of the nucleic acid as a reagent in molecular biological reactions, for example in PCR.

It is should be understood that although the present invention is preferably used for the isolation of high molecular weight DNA or BACs, it may also be used in the context of isolating other nucleic acids, for example, RNA, smaller molecular weight DNA, and the like.

High Molecular Weight Nucleic Acid Isolation Method
  Method

One embodiment of the present invention is a method for isolating high molecular weight DNA from a DNA containing starting material. The method can be performed on a single sample, i.e., within a microcentrifuge tube, or on a multitude of samples in a multi-well plate, e.g., 96 or 384 well plate, at the same or substantially the same time. The method includes mixing the starting material with a lysing and denaturing substance to release the DNA. The mixture is preferably vortexed for at least 5 seconds and allowed to incubate at from 60 to 75° C. for 1 to 10 minutes. The sample should be vortexed periodically. In preferred embodiments, the mixture is incubated in a Thermomixer (Eppendorf) at approximately 900 rpm and 70° C. for 10 minutes.

In preferred embodiments, the mixture is separated into a first portion and a second portion, where the first portion has the majority of the nucleic acid and the second portion contains the cell debris. Typically the separation is accomplished by centrifuging the sample from 1 to 5 minutes at from 12,000 to 16,000×g for a sample within a tube and from 1 to 30 minutes at from 500 to 2500×g for a sample within a well of a plate, and removing the supernatant to a fresh tube or corresponding well in a plate. Note, however, that in some cases the mixture does not require the separation of the cell debris from the nucleic acid, in which case the separation step is not required.

An alcohol and detergent substance is added to the first portion, or in cases where the mixture was not separated into two portions, to the mixture. The combination is vortexed for at least 5 seconds and transferred to a tube, or a well of a multi-well plate, containing a trapping membrane of the present invention. In preferred embodiments, the trapping membrane is incorporated into a housing that fits within a microcentrifuge tube and facilitates the insertion and removal of the trapping membrane from the microcentrifuge tube. This device is referred to as a spin device. The combination is allowed to incubate from zero to 2 minutes and preferably from 1 to 2 minutes. The precipitated nucleic acids are now trapped on the surface of the membrane.

Trapping of the nucleic acid on the membrane requires that the precipitated nucleic acid fully contact the membrane, as such, the precipitated nucleic acid may be centrifuged, or filtered (gravity or vacuum), i.e., pulled over, the membrane to enhance this contact. In preferred embodiments, the sample/trapping membrane are centrifuged together for 1 to 10 minutes at from 12,000 to 16,000×g in tubes, and at 500 to 2500×g in multi-well plates. Trapping the nucleic acid on the membrane, as opposed to pelleting the precipitated nucleic acid in the bottom of a tube or well, allows for superior separation of the nucleic acid from the cell derived contaminants. Precipitating the nucleic acid on the membrane allows the trapped nucleic acid to be washed on a platform via centrifugation or filtration, and allows the method to be further incorporated into high throughput applications, as discussed further below.

Depending on the anticipated application of the nucleic acid, the trapped nucleic acid may be washed one or more times with a wash buffer to remove contaminants associated with the nucleic acids or the trapping membrane. Typical wash buffer volumes are from 100 $\mu$l to 600 $\mu$l. Wash buffer may be separated from the membrane by filtering or centrifugation as discussed above. It should be noted that the membrane may be dried before proceeding to the next step to facilitate re-suspension of the nucleic acid.

The trapped nucleic acid is released from the trapping membrane by re-suspending the precipitated nucleic acid in an appropriate volume of re-suspension buffer and incubating at from about 50 to 70° C. for from about 3 to 5 minutes. The nucleic acid is now soluble and may be separated away from the trapping membrane with a brief centrifugation step (12,000 to 16,000×g for a tube or 500 to 2500×g for a plate, from about 1 to 3 minutes, and preferably for about 1 minute), or by filtration step, where the trapping membranes are incubated in the re-suspension buffer for 1 to 3 minutes before applying a vacuum to the membranes. Samples are collected in appropriate containers-tubes or wells of a plate. The release of the nucleic acid from the trapping membrane, using the methods of the present invention, is rapid and more effective than other re-suspension techniques on precipitated nucleic acid. For example, it is known that some level of irreversible binding occurs between gDNA and BACs to glass fiber membranes, resulting in loss of yield and slow re-suspension times (hours to days). In the present invention, the trapped nucleic acid, even large fragments of nucleic acid, are re-suspended and released from the membrane in 45 minutes, preferably in 30 minutes and most preferably in 10 minutes or less.

Note that the yield of nucleic acid may vary dependent on the starting material, and conditions under which the above methods are performed, however, it may be expected that from 3 to 12 $\mu$g nucleic acid per 200 $\mu$l sample of blood may be obtained.

Isolated nucleic acid may be analyzed by any well known means within the art, including taking $A_{260}/A_{280}$ ratios, separating the nucleic acid via gel electrophoresis, etc. In addition, the isolated nucleic acid from the present invention is suitable for use in any number of molecular biology reactions, including PCR, DNA ligation, etc. Reactions may be performed directly on the re-suspended nucleic acid sample where the sample is re-suspended at an appropriate concentration or may be re-precipitated and re-suspended in a more appropriate solution and/or concentration.

In preferred embodiments of the present invention the nucleic acid is genomic DNA, and in more preferred embodiments of the present invention the isolated nucleic acid is genomic DNA having at least 60%, more preferably 70%, and most preferably 80%, of the isolated gDNA at least 20 kb in molecular weight. In a most preferred embodiment of the present invention the isolated nucleic acid is genomic DNA having at least 60%, and more preferably 70%, of the isolated gDNA from 30 to 75 kb in molecular weight.

As previously noted, the above methods may be performed substantially simultaneously on two or more starting materials in a multi-well plate. In preferred embodiments, the methods of the present invention are further automated to allow the processing of numerous starting samples substantially simultaneously. Preferably, this is accomplished by precipitating the nucleic acids onto a nylon membrane located in the wells of a multi-well filter plate. Wash buffer is applied to each well, having the trapped nucleic acid, and a vacuum source activated to pull the wash buffer through the nylon membrane. The isolated nucleic acid is released from the membrane by incubating it with a re-suspension buffer and allowing the now soluble nucleic acid to be pulled into a new multi-well plate. The release and re-suspension of the nucleic acid is rapid compared to other known nucleic acid isolation methods and allows for the isolated nucleic acid to be immediately used in PCR reactions, sequencing reactions, restriction endonuclease reactions, and the like. In fact, the isolated nucleic acid may be released and re-suspended in any of a number of molecular biology compatible buffers, for example a buffer for direct use in a PCR reaction. These embodiments may be performed using plates having multiple sample containers, for example a 96 well plate or a 384 well plate, where the trapping membrane is placed at the bottom of each well, and the above described steps are performed substantially simultaneously within each well of the plate or plates.

Components

Starting Material

Starting materials have a target nucleic acid for isolation, for example blood, buffy coat, saliva, cell cultures, etc, where the most preferred starting material for use with the present invention is blood. In preferred embodiments, the starting material is a liquid from about 1 to 200 $\mu$l, and preferably from about 50 to 200 $\mu$l.

Lysing and Denaturing Substance

The lysing and denaturing substance of the invention causes the release of the nucleic acids from the intact cells of the starting material. Typically, the lysing and denaturing substance includes a buffering agent, a salt, a detergent and a protease. The combination of ingredients causes the digestion of proteins, inhibition of nucleases, and the solubilization of lipids, proteins and the like, and may result, to some extent, in the smaller nucleic acids, i.e., sheared gDNA, RNA, etc., to be precipitated out of solution, the mechanism of which has been described in U.S. Pat. No. 5,010,183.

Typically, the lysing and denaturing substance is added to the starting material to achieve a salt concentration in the range of about 2 to 4 M, and preferably in the range of about 2.5 to 3.5 M; a detergent concentration in the range of about 0 to 4%, and preferably in the range of about 1.5 to 2.5%; and a protease concentration in the range of about 50 to 1000 $\mu$g/ml, and preferably in the range of about 100 to 700 $\mu$g/ml. The buffering agent, typically Tris-HCL, is included at a concentration of about 10 mM, so as to maintain a pH of the mixture in the range of 7 to 8.5 and preferably in the range of 7.9 to 8.1.

In a preferred embodiment of the present invention, the lysing and denaturing substance includes fine particles, for example polyvinypyrrolildone, having a concentration in the range of about 0 to 5%, and preferably a range of about 3 to 4%.

In preferred embodiments of the lysing and denaturing substance, the salt is NaCl, NaOAc, KOAc, $NH_4Cl$, and the like, or mixtures thereof. The detergent is a quaternary amine cationic detergent, for example, cetyltrimethylammonium bromide (CTAB), and the like, and mixtures thereof, and the protease is Proteinase K.

Alcohol and Detergent Substance

The alcohol and detergent substance of the invention causes the precipitation of the nucleic acid from solution. Typically the alcohol and detergent substance contains an alcohol and a detergent, although in some circumstances the substance may only include an alcohol.

Typically the alcohol and detergent substance is added to the nucleic acid containing solution to achieve an alcohol concentration of from about 60 to 100%, and preferably from about 70 to 95%, and a detergent concentration of from about 0 to 40%, and preferably from about 5 to 30%.

In preferred embodiments of the alcohol and detergent substance, the alcohol is isopropanol, ethanol, and the like, and the detergent is Tween 20 and the like.

Trapping Membrane

The trapping membrane of the invention serves as a platform for the nucleic acid to be precipitated onto and thereby preferentially isolated from the solution. Membranes include glass fiber, glass fiber treated with hydrophobic and oleophobic coatings, nylon, and silica particles, and the like. The trapping membrane may be prepared as a spin column or spin device to facilitate the precipitation, washing and re-suspension steps of the present invention, or additionally, may be included within the wells of a trapping membrane plate, preferably a 96 well trapping membrane plate.

Wash Buffer

The wash buffer of the invention serves to gently separate the precipitated nucleic acid trapped on the membrane from associated protein, lipids and cell debris in general. Typically, the wash buffer includes a buffering agent, a salt, EDTA and can contain alcohol. Preferably, the salt is from 400 to 600 mM NaCl or the like, and the buffering agent is approximately 10 mM Tris-HCL. Typically the volume of wash buffer passed over the trapping membrane is sufficient to remove contaminants, but not of a volume to substantially effect the yield of the isolated nucleic acid.

Re-suspension Buffer

The re-suspension buffer of the invention serves to rapidly re-suspend and solubilize the trapped nucleic acid off of the membrane. Typically, the re-suspension buffer may be water, 10 mM Tris-HCL or 10 mM mM TE solution, although other solutions may be substituted, as long as a majority of the nucleic acid is soluble in the solution. For example, trapped nucleic acid may be directly released with a PCR compatible buffer so that PCR may be directly performed on the released nucleic acid.

High Molecular Weight Nucleic Acid Isolation Kit

Embodiments of the present invention provide kits for the performance of the above described nucleic acid isolation methods. In one embodiment of the present invention, the kit includes a lysis and denaturing substance, an alcohol and detergent substance, a wash buffer, a re-suspension buffer, and a trapping membrane. In a preferred embodiment the kit further includes molecular biology grade water and collection tubes. The kits of the present invention may also include any of the following: 384 well plates, 96 well plates, pipet tips, a thermomixer, a water bath, a heat block, blood collecting equipment, i.e., syringes, needles, anticoagulant, protective gloves, etc, and a microcentrifuge.

For maximum stability, the kits contain lyophilized protease, for example Proteinase K. Kits are believed to be stable for at least six months.

BAC Isolation Method

Method

Another embodiment of the present invention is a method for isolating BACs from a bacterial culture. The method includes growing a BAC containing culture overnight with shaking at 37° C. in individual wells of a 96 well culture plate (each well having a 2.0–2.4 ml capacity). Bacterial transformation protocols with BACs, formulations for bacterial growth media, and bacterial seeding densities are well known in the art. Note, the following method is illustrated using multiple cultures in 96 well plates, however, it is envisioned that the same method may be performed on one or more bacterial cultures using microcentrifuge tubes, 6 well plates, 24 well plates, 48 well plates, etc. Note also, the following method may be used to isolate other nucleic acids as well as BAC, for example, cosmids, plasmids, RNA and the like, which are all envisioned to be within the scope of the present invention.

96 well culture plates are centrifuged at from about 1000 to 2500×g for 2 to 10 minutes, and preferably are centrifuged at approximately 1900×g for 5 minutes. The centrifugation is performed at room temperature in a swinging bucket centrifuge (Eppendorf model 5810 with Deep Well Plate Rotor). Cell supernatant is removed, either by decanting or aspiration, to ensure that the cell pellets remain at the bottom of each well of the 96 well plate. Note that in preferred embodiments, the cell volume should be sufficient to achieve 5 to 20 $OD_{600}$ units.

Approximately 150 to 250 $\mu$l of a BAC cell resuspension substance is added to each cell pellet. The pellets are re-suspended by vortexing or other method until the pellets are completely dispersed. Approximately 150 to 250 $\mu$l of substance is added to each well. A Plate Seal is placed on the 96 well plate, which is then mixed by inversion from 1 to 10 times, preferably for 5 times, and incubated from 1 to 10 minutes at room temperature, preferably 5 minutes.

Release of the BAC from the bacterial cultures continues by removing the Plate Seal and adding approximately 150 to 250 $\mu$l of potassium acetate solution, preferably cold (4° C.), to each culture in the 96 well plate. The Plate Seal is replaced, and the plate is mixed by inversion from 5 to 15 times, preferably 10 times, or by other mixing means.

A 96 well filter plate (Eppendorf-5 Prime) is placed directly over a second 96 deep well culture plate. Each well of the 96 well filter plate includes a filter for separating out the bacterial cell debris, while allowing the soluble BACs to pass through.

Contents from each well of the first 96 well culture plate are transferred to the corresponding well of the 96 well filter plate. In preferred embodiments, a vacuum manifold is used to pull the samples through the 96 well filter plate and into the corresponding deep wells of a second 96 well culture plate or directly into a 96 well trapping plate (see below).

Approximately from 150 to 250 $\mu$l of an alcohol and detergent substance is added to the filtered contents from above. If the contents are still within a 96 well culture plate they are transferred to the corresponding well of the 96 well trapping plate and the mixture is allowed to incubate from 1 to 10 minutes, and preferably 5 minutes, at room temperature. This precipitates the BACs in each solution.

A 96 well trapping plate is prepared having a trapping membrane of the present invention inserted into each well. The trapping membrane acts as a platform to trap the precipitated BACs and allow for removal of the BAC associated contaminants (as above for gDNA method). In preferred embodiments, a second membrane of the invention may be placed adjacent to and under the trapping membrane to facilitate the flow properties of the trapping membrane as well as to lend support under the trapping membrane.

Preferred embodiments include a vacuum manifold to facilitate the precipitation of the BACs onto the trapping membrane of the 96 well trapping plate, while the supernatant is passed into corresponding wells of a third 96 well plate to be discarded.

In preferred embodiments, approximately 800 to 2400 $\mu$l of wash buffer, and preferably from 1200 to 2000 $\mu$l of wash buffer, is added to each well of the 96 well trapping plate to ensure that BAC associated contaminants are removed from the trapping membrane. The wash step may be repeated one or more times, preferably 2 times.

In a preferred embodiment, a vacuum is maintained, for approximately 15 to 20 minutes, on the 96 well trapping plate to remove any residual wash solution from the wells. The 96 well trapping plate may be removed from the vacuum manifold and the bottom surface of the plate blotted on a paper towel to ensure that no residual fluids remain associated with the samples.

The 96 well trapping plate is placed over a 96 well collection plate (Eppendorf-5 Prime). Approximately from 50 to 100 $\mu$l of a re-suspension buffer is added to each well of the 96 well trapping plate and allowed to incubate from 1 to 10 minutes at room temperature, and preferably from 3 to 7 minutes at room temperature. The volume of the re-suspension buffer may be modified to allow for a more concentrate or dilute BAC containing solution, dependent on the BACs use. A vacuum is slowly applied to the filter plate over a period of 1 to 15 minutes, and preferably from about 9 to 11 minutes. Alternatively, the plate assembly (trapping plate and collection plate) can be centrifuged from about 500 to 1900×g for 5 to 10 minutes, and preferably are centrifuged from 10 minutes, at room temperature. The collection plate containing the isolated BACs is stored at 4° C. Note, as discussed above, the release of BAC from the membrane is rapid, and allows for the immediate use of the BAC in PCR reactions, DNA sequencing reactions, and the like Isolated BAC may be analyzed by any of the well known means within the art, including BAC end sequencing and DNA fingerprint analysis. Reactions may be performed directly on the re-suspended BAC samples or may be re-precipitated and re-suspended in a more suitable buffer or at a more suitable concentration.

In preferred embodiments, the methods above are automated to allow for the processing of numerous 96 well sample plates during the course of a day, i.e., high throughput. The automated processing of numerous BAC samples is vacuum driven throughout the course of the isolation method. This allows for the convenient processing of numerous starting samples on a vacuum manifold at substantially the same time. Note that other multi-well plates, for example a 384 well plate, are envisioned to be within the scope of the present methods and are especially useful in the vacuum driven high throughput applications of the invention.

Components

Starting Material

Starting materials for the BAC isolation methods include bacterial cultures transformed to include BACs. Typically the bacteria is *E. Coli*. BAC sizes for use with the present invention range from 30 to 300 kb, and are preferably from 75 kb to 225.

BAC Cell Resuspension Substance

The cell resuspension substance of the invention participates in the release of the BAC from the bacterial cells and degrades RNA. Typically, the cell resuspension substance includes a buffering agent, typically Tris-HCL, RNase A, and EDTA.

Typically the RNase A substance is added to the bacterial cultures to achieve a RNase A concentration of from about 50 to 150 $\mu$g/ml, and preferably from about 80 to 120 $\mu$g/ml, an EDTA concentration of from about 1 to 20 mM, and preferably from 8 to 12 mM, a buffering agent concentration of from about 40 to 60 mM, and an egg white lysozyme concentration from about 650 to 950 $\mu$g/ml.

Lysis Substance

The lysis substance of the invention also participates in the release of BAC from the bacterial cultures. Typically the lysis substance contains an anionic detergent and a strong base.

Typically the anionic detergent is added to the bacterial cultures to achieve a concentration of from about 0.5 to 1.5%, and preferably from about 0.8 to 1.2%, and a base concentration of from about 0.05 to 0.35 mM, and preferably from about 0.15 to 0.25 M.

In preferred embodiments of the lysis substance, the anionic detergent is SDS and the base is NaOH, and the like.

Neutralization Substance

The neutralization substance participates in the release of BAC from bacterial cultures. The neutralization substance typically contains potassium acetate from about 2.5 to 3.5 M, and a concentration of acetic acid from about 1.5 to 2.5 M.

Alcohol and Detergent Substance

The alcohol and detergent substance of the invention causes the precipitation of the BACs from solution. Typically the alcohol and detergent substance contains an alcohol and a detergent, although in some circumstances the substance may only include an alcohol.

Typically the alcohol and detergent substance is added to the BAC containing solution at an alcohol concentration of from about 60 to 100%, and preferably from about 70 to 95%, and a detergent concentration of from about 0 to 40%, and preferably from about 5 to 30%.

In preferred embodiments of the alcohol and detergent substance, the alcohol is isopropanol, ethanol, and the like, and the detergent is Tween 20, Tween 80, IGEPAL CA 630, and the like.

Trapping Membrane

The trapping membrane of the invention serves as a platform for the precipitated BAC to be trapped on and around and thereby preferentially collected from the solution. Preferably membranes include nylon, glass fiber, glass fiber treated with hydrophobic and oleophobic coatings, silica particles, and the like.

The second membrane of the invention serves to support the trapping membrane and to facilitate the flow of the wash buffer and re-suspension buffer through the trapping membrane when the trapping membrane is positioned within a well of a multi-well plate. Preferable second membranes include melt-blown polypropylene with 25 micron pores (MBPP-25), and the like.

Wash Buffer

The wash buffer of the invention serves to gently separate the precipitated BAC trapped on the membrane from associated protein, lipids cell debris in general, and detergents. Typically, the wash buffer includes a buffering agent, a salt, an alcohol and EDTA. Preferably, the salt is about 60 mM NaCl or the like, the EDTA about 0.6 mM, the alcohol about 30% and the buffering agent about 6 mM. In concentrated form, the wash buffer is stored as a solution having 150 to 250 mM NaCl, EDTA is from about 1.5 to 2.5 mM, the alcohol is about 70%, and the buffering agent is 15 to 25 mM Tris-HCL. Typically the volume of wash buffer passed over the trapping membrane is sufficient to remove contaminants, but not of a volume to substantially effect the yield of the isolated nucleic acid.

Re-suspension Buffer

The re-suspension buffer of the invention serves to re-suspend and solubilize the trapped BAC off of the membrane. Typically the re-suspension buffer may be water or a 10 to 50 mM Tris-HCL solution, and the like, although other solutions may be substituted, as long as a majority of the BAC is soluble in the solution. For example, DNA sequencing buffers may be used to release and re-suspend the BAC, thereby allowing for the immediate sequencing of the BAC.

BAC Isolation Kit

Embodiments of the present invention provide kits for the performance of the above described BAC isolation methods. In one embodiment of the present invention the kit includes a lysis substance, resuspension substance, neutralization substance, an alcohol and detergent substance, a wash buffer, a re-suspension buffer, and a 96 well trapping plate. In a preferred embodiment the kit further includes a 96 well filter plate, molecular biology grade water and collection tubes. The kits of the present invention may also include any of the following: 96 well plates, pipet tips, a vacuum manifold, and *E. coli* growth media.

Having generally described the invention, the same will be more readily understood by reference to the following examples, which are provided by way of illustration and are not intended as limiting.

EXAMPLES

Example 1

High Purity and Molecular Weight DNA Result from gDNA Isolation Method

Materials and Methods

Approximately 200 µl of human blood was treated with 20 µl reconstituted Proteinase K and 350 µl of 3 M Ammonium chloride, 2% w/v cetyltrimethylammonium bromide, 4% polyvinypyrrolidone and 10 mM Tris-HCL, pH 8 in a 1.5 ml microfuge tube. Blood samples were obtained and preserved with heparin, sodium citrate and EDTA. The mixture was vortexed on high for approximately 5 seconds and incubated in a Thermomixer at 70° C., 900 rpm, for 10 minutes. The tubes were then removed and centrifuged for 3 minutes at 12,000 to 16,000×g. Tubes were removed and supernatant poured into a fresh microcentrifuge tube.

Approximately 200 µl of alcohol and detergent substance, (70% isopropanol and 30% Tween 20) was added to the supernatant and the sample was vortexed for 5 seconds. The sample was added to a microcentrifuge tube containing a trapping membrane of the present invention, where the sample was incubated for approximately 1 minute at room temperature. The sample containing the membrane was centrifuged for 2 minutes at 12,000 to 16,000×g and the flowthrough decanted.

Approximately 600 µl of a wash buffer (60 mM Tris-Cl pH 8, 3 mM EDTA pH 8, 150 mM NaCl and 30% ethanol) was placed over the membrane and centrifuged for 1 minute at 12,000 to 16,000×g. The flowthrough was decanted and approximately 400 µl of wash buffer was placed over the membrane. The membrane and wash buffer was centrifuged for 3 minutes at 12,000 to 16,000×g. The membrane was removed to a new microcentrifuge tube.

Approximately 200 µl resuspension buffer, (10 mM Tris-HCL, pH 8) was incubated on the membrane for 3 minutes at 70° C. The solution was centrifuged for 1 minute at 12,000 to 16,000×g to elute the gDNA.

Genomic DNA samples were also isolated, for comparison sake, using the Qiagen kit.

Purity and concentration of the isolated gDNA was determined taking a ratio of sample absorbance at 260 nm to 280 nm, noting that a $A_{260}/A_{280}$ ratio of 1.6 to 1.8 illustrates a highly purified sample of DNA.

Analysis of gDNA integrity was performed by running isolated gDNA on a 0.6% agarose gel (see FIG. 1).

Results and Discussion

As illustrated in FIG. 1, isolation of gDNA from blood using the methods of the present invention resulted in a vast majority of the gDNA being isolated in molecular weight sizes above 23 kb (lanes 2–9). In fact, the data shows that only approximately 20% of the total density of DNA in the samples are ≦23 kb, indicating that the isolation technique did not generate a high percentage of shearing. Further, the isolated gDNA is of a high purity, having a $A_{260}/A_{280}$ ratio of 1.6 to 1.8.

In contrast, conventional gDNA isolation techniques typically result in a higher percentage of total DNA being ≦23 kb size range. In a side-by-side comparison, gDNA isolated using the Qiagen kit resulted in approximately 40% of the total density of DNA being ≦23 kb (lanes 10–17).

This data illustrates that the gDNA isolation method provides a powerful tool for isolating high molecular weight gDNA that minimizes the shearing of the DNA, and that the isolated gDNA has a minimal amount of contaminants.

Example 2

High Yield Results from gDNA Isolation Method

Materials and Methods

The materials and methods discussed in Example 1 were used to test the yields of gDNA obtained from varying amounts of sample as well as to test the reproducibility of the method on a number of similarly treated samples.

Results and Discussion

The data illustrated in Table 1 shows that 200 µl samples of blood may yield between about 3 and 12 µg of gDNA. The data was reproducible, as shown by the corresponding standard deviations, and the purity respectable, 1.6 to 1.8 range.

Figure 2:
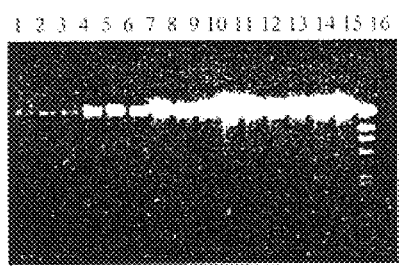
FIG. 2 illustrates gDNA isolated from 10 (lanes 1–3) to 200 μl (lanes 13–15) blood in accordance with a method of the present invention. Lane 16 has λ Hind III Marker, and lanes 4–12 show increasing amounts of blood from which the gDNA was isolated.
Figure 3:
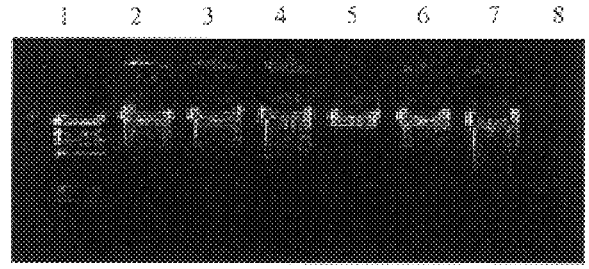
FIG. 3 illustrates gDNA isolated from chicken blood in accordance with a method of the present invention. Lane 1 shows λ Hind III Marker, lanes 2–5 show gDNA isolated from 5 μl chicken blood and lanes 6–8 show gDNA isolated from 10 μl chicken blood.
Figure 4:
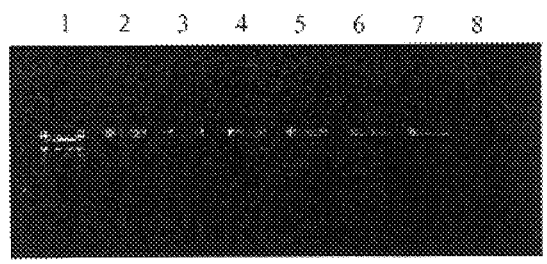
FIG. 4 illustrates gDNA isolated from rat blood in accordance with a method of the present invention. Lane 1 shows λ Hind III Marker, lanes 2–5 show gDNA isolated from 5 μl rat blood and lanes 6–8 show gDNA isolated from 10 μl rat blood.
Figure 5:
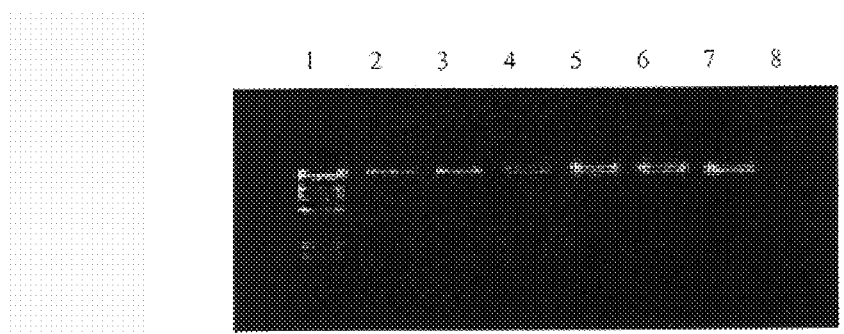
FIG. 5 illustrates gDNA isolated from fresh bovine blood in accordance with a method of the present invention. Lane 1 shows λ Hind III Marker, lanes 2–5 show gDNA isolated from 5 μl bovine blood and lanes 6–8 show gDNA isolated from 10 μl bovine blood.
Figure 6:
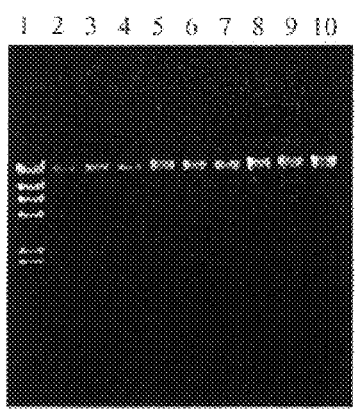
FIG. 6 illustrates gDNA isolated from frozen bovine blood in accordance with a method of the present invention. Lane 1 shows λ Hind III Marker, lanes 2–4 show gDNA isolated from 10 μl frozen bovine blood, lanes 5–7 shown gDNA isolated from 25 μl frozen bovine blood, and lanes 8–10 show gDNA isolated from 50 μl frozen bovine blood.

As shown in FIG. 2, isolated gDNA from a sample as small as 10 µl (lanes 1–3) can be visualized on an ethidium bromide stained agarose gel, as well as samples from 50 µl (lanes 4–6), 100 µl (lanes 7–9), 150 µl (lanes 10–12) and 200 µl (lanes 13–15)

This data illustrates the utility of using the gDNA isolation method for testing very small sample sizes, while maintaining purity and reproducibility.

TABLE 1

|  | Sample # | Average Yield ($\mu$g) | Average OD$_{260/280}$ |
|---|---|---|---|
| Fresh Blood | 1 | 5.11 (±0.39) | 1.76 (±0.04) |
|  | 2 | 5.45 (±0.41) | 1.70 (±0.09) |
|  | 3 | 7.13 (±0.87) | 1.74 (0.03) |
|  | 4 | 6.93 (±0.74) | 1.76 (±0.02) |
| Averages (n = 8) | n/a | 6.16 | 1.74 |

Example 3 gDNA Isolation Method is Useful on Various Types of Starting Materials

Materials and Methods

The materials and methods discussed in Example 1 were used to analyze the ability of the gDNA isolation method to isolate high molecular weight gDNA from fresh chicken blood, rat blood, and bovine blood, as well as from a frozen sample of bovine blood. Fresh samples were taken from the appropriate animal and blood stored in either heparin or EDTA. The frozen sample was stored at −20° C. and thawed 15 minutes prior to the gDNA isolation method.

Results and Discussion

Chicken (FIG. 3), rat (FIG. 4), and bovine (FIGS. 5 and 6) blood were tested using the gDNA isolation method for DNA quality, as shown in FIGS. 3–6. As was the case using human blood, gDNA isolated from each of the fresh blood types resulted in a high degree of high molecular weight species, and a minimal amount of smaller and presumably sheared DNA species. In addition, the gDNA isolated from the frozen bovine blood (FIG. 6) was also of predominately high molecular weight, showing little or no difference compared to the fresh samples. In the Figures, lanes 2–5 represent 5 $\mu$l sample, and lanes 6–8 represent a 10 $\mu$l sample, except in FIG. 6, where lanes 2–4 is 10 $\mu$l, lanes 5–7 is 25 $\mu$l, and lanes 8–10 is 50 $\mu$l.

This data illustrates the utility of the present invention for use on gDNA isolation from a multitude of species, including human (Examples 1 and 2), rat, chicken, and bovine.

Example 4

DNA Isolated Using the gDNA Isolation Method is Suitable for PCR

Materials and Methods

The materials and methods discussed in Example 1 were used to isolate gDNA for subsequent use in PCR applications. Several different starting materials were used as a DNA source, including fresh and frozen blood. An alternative series of PCR reactions were performed on gDNA isolated using the Qiagen kit.

Isolated gDNA samples were prepared for PCR by mixing 50 ng isolated genomic DNA with human β globin primers to amplify 2 kb fragments. PCR products were run on a 1% agarose gel and stained with ethidium bromide, as is well known in the art.

Results and Discussion

Figure 7:
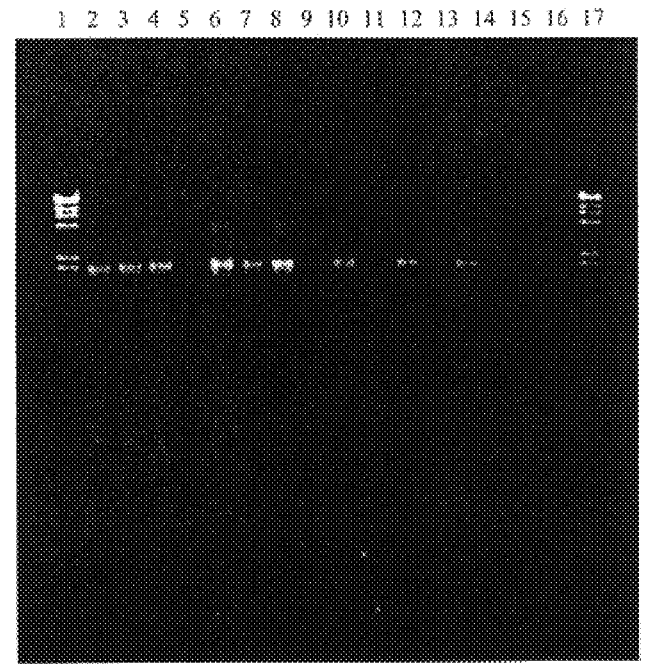
FIG. 7 illustrates 2 kb PCR reaction products from PCR experiments using gDNA isolated in accordance with a method of the present invention. Lane 1 shows λ Hind III Marker; lane 2 shows PCR reaction products from gDNA isolated from a fresh blood sample using the methods of the present invention; lane 3 shows PCR reaction products from gDNA isolated from fresh blood sample using Qiagen kit; lane 4 shows PCR reaction products from gDNA isolated from 5.5 month old blood using the methods of the present invention; lane 5 shows PCR reaction products from gDNA isolated from 5.5 month old blood using Qiagen kit; lane 6 shows PCR reaction products from gDNA isolated from a freshly frozen blood sample using the methods of the present invention; lane 7 shows PCR reaction products from gDNA isolated from a freshly frozen blood sample using the Qiagen kit; lane 8 shows PCR reaction products from gDNA isolated from a 1 month old frozen blood sample using the methods of the present invention; lane 9 shows PCR reaction products from gDNA isolated from a one month old frozen blood sample using the Qiagen kit; lane 10 shows PCR reaction products from gDNA isolated from a citrate preserved blood sample using the methods of the present invention; lane 11 shows PCR reaction products from gDNA isolated from a citrate preserved blood sample using the Qiagen kit; lane 12 shows PCR reaction products from gDNA isolated from a heparin preserved blood sample using the methods of the present invention; and lane 13 shows PCR reaction products from gDNA isolated from a heparin preserved blood sample using the Qiagen kit. Lanes 14–17 are control lanes.

Isolated gDNA from the gDNA isolation method of the present invention provides an excellent template for PCR reactions. As shown in FIG. 7, PCR reactions performed on a number of different gDNA templates resulted in the production of the expected PCR products, i.e., the PCR products were of the expected size and, as indicated by their staining, of high quantity (lanes 2, 4, 6, 8, 10, and 12). In comparison, gDNA isolated using the Qiagen kit consistently yielded lower amounts of PCR product, and in particular, larger inhibition was seen with increased amounts of template, suggesting that the isolated template DNA contained PCR inhibitors (lanes 3, 5, 7, 9, 11, and 13).

Inhibitors of PCR are common in samples recovered from many blood gDNA kits. In particular, hemoglobin is a strong inhibitor of PCR. The data shown in FIG. 7 illustrates that the gDNA isolation methods of the present invention are useful for providing PCR template quality DNA. The isolated DNA would appear to be void or substantially void of PCR inhibitors.

Example 5

DNA Isolated Using the gDNA Isolation Method is Suitable for Restriction Analysis Materials and Methods The materials and methods discussed in Example 1 were used to isolate gDNA for subsequent use in restriction enzyme digests. Approximately 250 ng of purified gDNA was digested in a 20 $\mu$l reaction using 2 and 5 units of Sau3A I (New England Biolabs) at 37° C. for one hour. Digest products were run on a 1% agarose gel and stained using ethidium bromide. An alternative series of restriction digests were carried out on gDNA isolated using the Qiagen kit.

Results and Discussion

Figure 8:
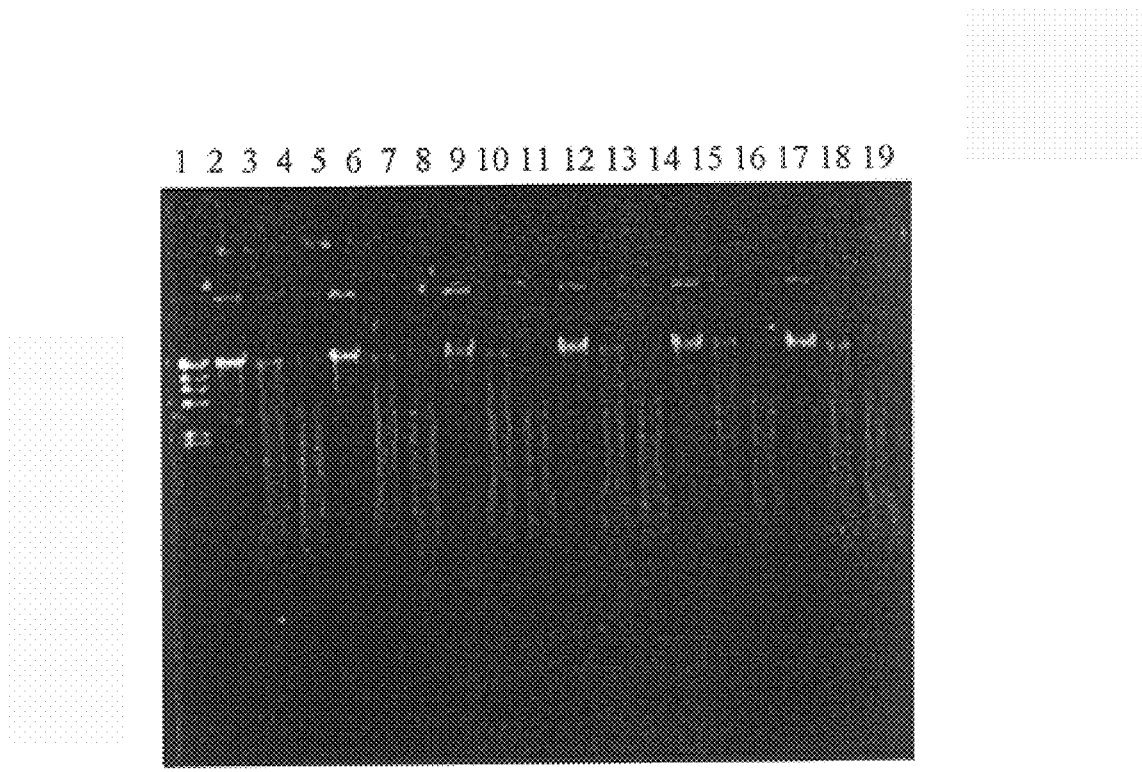
FIG. 8 illustrates restriction digest products from restriction digest experiments using gDNA isolated in accordance with a method of the present invention. Lane 1 shows λ Hind III Marker, lanes 2–10 shows restriction digest products on gDNA isolated using a Qiagen kit and lanes 11–19 shows restriction digest products on gDNA isolated using methods of the present invention.

Isolated gDNA from the gDNA isolation method of the present invention provides an excellent source of DNA for restriction digests. As shown in FIG. 8, gDNA isolated using the methods of the present invention was fully cut by the Sau3A I restriction enzyme (lanes 11–19).

This data illustrates that the gDNA isolation methods of the present invention are useful in preparing gDNA suitable for use in restriction digests. The isolated gDNA would appear to be void or substantially void of restriction digest inhibitors.

Example 6

Potential High Molecular Weight BAC Recovery from BAC Isolation Method

Materials and Methods

*E coli* cultures were transformed with a variety of different sized BAC constructs (a 112 kb human BAC, a 150 rice BAC, a 162 kb human BAC, and a 222 kb human BAC) as is well known in the art. Each transformed culture (approximately 1.5 mls) was grown overnight with shaking at 37° C. in a 96 well culture plate (Matrix catalog no. 18414). 96 well plates were centrifuged at 1900×g for 5 minutes at room temperature in a swinging bucket centrifuge (Eppendorf model 5810 with Deep Well Plate Rotor) and the culture supernatant was decanted.

Approximately 200 $\mu$l of BAC cell resuspension substance, 50 mM Tris-HCL, pH 7.6, 10 mM EDTA pH 8, 100 $\mu$g/ml Pancreatic RNase A, and 800 $\mu$g/ml Egg White Lysozyme, was added to each cell pellet and the cells were resuspended by vortexing until pellets are completely dispersed (Multi Tube Vortexer, VWR catalog no. 58816-115). Note that the 96 well plates are covered with a plate seal (Eppendorf-5 Prime Plate Seal).

Approximately 200 $\mu$l 200 mM NaOH, 1% SDS was added to each well for lysing the cells. Plates were inverted 5 times and the samples were incubated for 5 minutes at room temperature. Approximately 200 $\mu$l cold (4° C.) neutralization buffer (3 M Potassium Acetate, 2 M Acetic Acid, pH 5.2) was added to each well and the plates inverted an additional 10 times.

BAC containing mixtures were passed through a 96 well filter plate having a 10–20 µM glass fiber in each well to facilitate filtration of cell debris from the BAC. A vacuum was applied to each well to help draw the contents through the glass fiber filter. Supernatant was collected in a clean 96 well plate.

Approximately 200 µl of alcohol and detergent substance (5% Tween, 90% isopropanol) was added to each well. A 96 well plate having a GF/F membrane over MBPP (pore size of 20–25 µm) membrane in each well was prepared and the mixture added to each corresponding well where it is incubated for 5 minutes at room temperature.

A vacuum was applied and the filtrate discarded. A wash of 600 µl 200 mM NaCl, 20 mM Tris-HCL pH 7.2, 2 mM EDTA pH 8 diluted to 30% in ethanol was passed through each well of the 96 well plate by applying a vacuum. The filtrate was discarded and the wash repeated two more times.

Approximately 70 µl of re-suspension buffer (10 mM Tris-HCL at pH 8) was added to each well of the 96 well plate. The plate assembly was incubated for 5 minutes at room temperature and then centrifuged at 500×g for 40 minutes at room temperature. Elution is collected in a new 96 well plate, which is promptly covered with a plate seal. Samples contain BAC for analysis.

Isolated BAC were analyzed by running the product on 1% agarose gels and staining with ethidium bromide.

Results and Discussion

Figure 9:
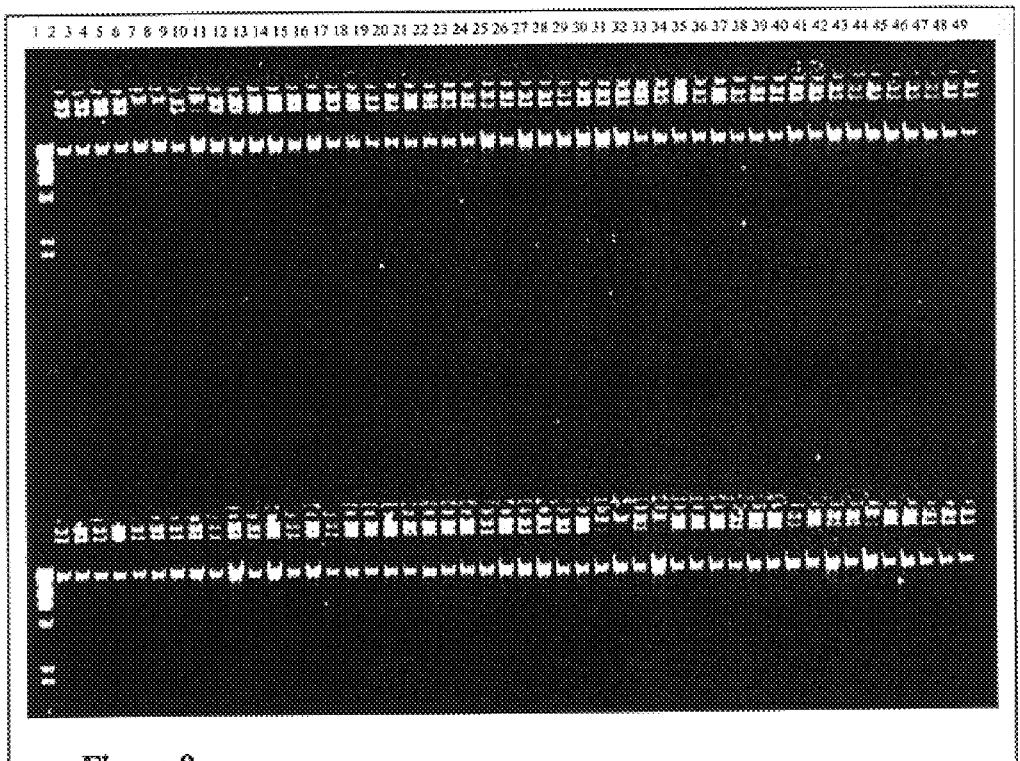
FIG. 9 illustrates a large number of isolated BACs from a mult-wll plate and using the methods of the present invention.

Isolated BAC from the BAC isolation method of the present invention provides highly pure and intact BAC, as is shown in FIG. 9. As such, the data illustrates that the methods of the present invention are useful in preparing BAC from transformed bacterial cultures.

It will be clear that the invention is well adapted to attain the ends and advantages mentioned as well as those inherent therein. While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims.

The entire disclosure and all publications cited herein are hereby incorporated by reference.

What is claimed is:

1. A method for isolating nucleic acid from a nucleic acid containing starting material, comprising:

mixing the starting material with a lysing and denaturing substance for release of the nucleic acid from the starting material;

separating the mixture into a first portion and a second portion, the first portion having a greater amount of the nucleic acid than the second portion;

adding an alcohol and detergent substance to the first portion of the mixture to precipitate the nucleic acid onto a nylon trapping membrane;

washing the nylon trapping membrane to remove nucleic acid and trapping membrane associated contaminants; and adding a re-suspension buffer to the nylon trapping membrane to rapidly re-suspend and release the nucleic acid from the nylon trapping membrane.

2. The method of claim 1 wherein the nucleic acid is re-suspended and released from the nylon trapping membrane in less than 10 minutes.

3. The method of claim 1 wherein the lysing and denaturing substance comprises a salt, a detergent, and a protease.

4. The method of claim 3 wherein the detergent is a quaternary amine cationic detergent.

5. The method of claim 4 wherein the quaternary amine cationic detergent is cetyltrimethylammonium bromide.

6. The method of claim 3 wherein the salt is selected from the group consisting of $NH_4Cl$, NaCl, NaOAc, and KOAc.

7. The method of claim 1 wherein the alcohol and detergent substance is added to achieve an alcohol concentration in the range of about 60 to 100% (v/v).

8. The method of claim 7 wherein the alcohol and detergent substance is added to achieve a detergent concentration in the range of about 1 to 30% (v/v).

9. The method of claim 1 wherein the starting material is whole blood.

10. The method of claim 1 wherein the nucleic acid is genomic DNA.

11. The method of claim 1 wherein the nucleic acid is plasmid DNA.

12. The method of claim 1 wherein the nucleic acid is cosmid DNA.

13. The method of claim 10 wherein over 70% of the isolated genomic DNA is greater than 20 kb in molecular weight.

14. The method of claim 13 wherein over 75% of the isolated genomic DNA is greater than 20 kb in molecular weight.

15. The method of claim 1 further comprising using the nucleic acid re-suspended in the re-suspension buffer in a PCR application.

16. The method of claim 1 wherein the re-suspending and releasing of the nucleic acid is in a PCR compatible buffer.

17. The method of claim 1 wherein nucleic acids from two or more starting materials are simultaneously isolated.

18. The method of claim 1 wherein the isolation of nucleic acid from the starting material is performed in a multi-well plate having the nylon trapping membrane in at least one well of the multi-well plate.

19. The method of claim 18 wherein the multi-well plate has 96 wells.

20. The method of claim 18 wherein the multi-well plate has 384 wells.

21. The method of claim 1 wherein the washing of the nylon trapping membrane comprises:

pulling wash buffer over the nylon trapping membrane using a vacuum.

22. The method of claim 21 wherein the re-suspending of the nucleic acid comprises:

pulling re-suspension buffer over the nylon trapping membrane using a vacuum.

23. The method of claim 1 wherein the nylon trapping membrane is incorporated into a spin device.

24. The method of claim 7 wherein the alcohol is selected from the group consisting of isopropanol, ethanol, and methanol.

25. A kit for isolating nucleic acid from a nucleic acid containing starting material comprising:

a lysing and denaturing substance in an amount sufficient to release the nucleic acid from the starting material;

an alcohol and detergent substance in an amount sufficient to precipitate the nucleic acid from the starting material; and a nylon membrane in an amount sufficient to trap the precipitated nucleic acid.

26. The kit of claim 25 further comprising a 96 well plate, wherein the nylon membrane is positioned within at least one well of the 96 well plate.

27. The kit of claim 25 wherein the nylon membrane is positioned within each well of the 96 well plate.

28. The kit of claim 25 wherein the lysing and denaturing substance comprises a salt, a cationic detergent and a protease.

29. The kit of claim 25 further comprising a 384 well plate, wherein the nylon membrane is positioned within at least one well of the 384 well plate.

30. A method for isolating bacterial artificial chromosomes from a bacterial artificial chromosome containing cell culture starting material, comprising:

mixing the starting material with a lysis substance for release of the bacterial artificial chromosomes from the cell culture;

passing the mixture through a pre-filter to remove cell debris from the bacterial artificial chromosomes;

adding an alcohol and detergent substance to the bacterial artificial chromosome containing filtrate to precipitate the bacterial artificial chromosomes onto a trapping membrane;

washing the trapping membrane with a purification solution to remove bacterial chromosome associated contaminants from the trapping membrane; and re-suspending the isolated bacterial artificial chromosome in a re-suspension buffer.

31. The method of claim 30 further comprising a second membrane supporting the trapping membrane, the second membrane comprising a synthetic polymer to facilitate liquid flow through the trapping membrane.

32. The method of claim 30 wherein the starting material contains bacterial artificial chromosomes from two or more cell cultures.

33. The method of claim 31 wherein the trapping membrane is positioned within a well of a multi-well plate and further comprises pulling a vacuum through the multi-well plate to facilitate trapping the bacterial artificial chromosomes on the trapping membrane.

34. The method of claim 33 wherein the multi-well plate has 96 openings.

35. The method of claim 33 wherein the trapping membrane is nylon.

36. The method of claim 31 wherein the second membrane is polypropylene having a pore diameter of from 20 to 30 microns.

37. The method of claim 30 wherein the alcohol and detergent substance is added to achieve an alcohol concentration in the range of about 70 to 100% (v/v).

38. The method of claim 37 wherein the alcohol is selected from the group consisting of isopropanol, ethanol, and methanol.

39. The method of claim 30 wherein the trapping membrane is a glass fiber treated with an oleophobic coating.

40. The method of claim 30 wherein the trapping membrane is a glass fiber.

41. The method of claim 30 further comprising performing a DNA sequencing reaction directly on the isolated BAC.

42. The method of claim 41 wherein the DNA sequencing reaction is immediately performed on the re-suspended and isolated BAC.

* * * * *